(12) United States Patent
Holder et al.

(10) Patent No.: US 11,006,881 B2
(45) Date of Patent: May 18, 2021

(54) DETECTING ACTIVITY IN PERIPHERAL NERVES

(71) Applicant: UCL Business Ltd, London (GB)

(72) Inventors: David Holder, London (GB); Kirill Aristovich, London (GB)

(73) Assignee: UCL Business Ltd, London (GB)

(*) Notice: Subject to any disclaimer, the term of this patent is extended or adjusted under 35 U.S.C. 154(b) by 473 days.

(21) Appl. No.: 15/567,537

(22) PCT Filed: Apr. 20, 2016

(86) PCT No.: PCT/GB2016/051092
§ 371 (c)(1),
(2) Date: Oct. 18, 2017

(87) PCT Pub. No.: WO2016/170327
PCT Pub. Date: Oct. 27, 2016

(65) Prior Publication Data
US 2018/0092560 A1 Apr. 5, 2018

(30) Foreign Application Priority Data

Apr. 21, 2015 (GB) ............................ 1506760
Jun. 2, 2015 (GB) ............................ 1509503

(51) Int. Cl.
*A61B 5/0536* (2021.01)
*A61B 5/24* (2021.01)
(Continued)

(52) U.S. Cl.
CPC .............. *A61B 5/24* (2021.01); *A61B 5/0536* (2013.01); *A61B 5/0809* (2013.01);
(Continued)

(58) Field of Classification Search
CPC ........ A61B 2503/40; A61B 2562/0209; A61B 2562/043; A61B 2562/164;
(Continued)

(56) References Cited

U.S. PATENT DOCUMENTS 5,919,142 A * 7/1999 Boone .................. A61B 5/0522
600/547
9,603,538 B2 * 3/2017 Fisher ................ A61B 5/04001
(Continued)

FOREIGN PATENT DOCUMENTS

WO WO 2009/068961 A2 6/2009
WO WO 2010/128326 A1 11/2010
WO WO 2014/205407 A2 12/2014

OTHER PUBLICATIONS

DS Holder, "Impedance changes during evoked nervous activity in human subjects: implications for the application of applied potential tomography to imaging neuronal discharge", Clinical Physics and Physiological Measurements 10(3):267-274 (1989) (Year: 1989).*
(Continued)

*Primary Examiner* — Eun Hwa Kim
(74) *Attorney, Agent, or Firm* — Myers Bigel P.A.

(57) ABSTRACT

There is disclosed a method of determining electrical properties in a peripheral nerve of a human or animal subject using a plurality of electrodes spaced around a perimeter of the nerve, by applying a probe electrical signal to each of a plurality of combinations of the electrodes, and using the resulting electrical responses to determine the electrical properties, for example by carrying out an electrical impedance tomography image reconstruction.

20 Claims, 8 Drawing Sheets

(51) Int. Cl.
    *A61B 5/08*    (2006.01)
    *A61B 5/00*    (2006.01)
(52) U.S. Cl.
    CPC .......... *A61B 5/6877* (2013.01); *A61B 5/6884*
            (2013.01); *A61B 5/7278* (2013.01); *A61B*
                *2503/40* (2013.01); *A61B 2562/0209*
            (2013.01); *A61B 2562/043* (2013.01); *A61B*
            *2562/164* (2013.01); *A61B 2576/00* (2013.01)
(58) Field of Classification Search
    CPC ............ A61B 2576/00; A61B 5/04001; A61B
            5/0809; A61B 5/6877; A61B 5/6884;
            A61B 5/7278; A61B 5/0536; A61B 5/24;
            A61N 1/36071; A61N 1/37223; A61N
                                    1/36167
    See application file for complete search history.

(56) References Cited

U.S. PATENT DOCUMENTS

| | | | |
|---|---|---|---|
| 2004/0249429 A1 | 12/2004 | Tadlock | |
| 2006/0041277 A1* | 2/2006 | Deem | A61N 1/36128 607/3 |
| 2007/0239243 A1* | 10/2007 | Moffitt | A61N 1/0558 607/118 |
| 2008/0147141 A1* | 6/2008 | Testerman | A61N 1/0556 607/48 |
| 2008/0300655 A1 | 12/2008 | Cholette | |
| 2010/0010369 A1* | 1/2010 | Pomfrett | A61B 5/0042 600/554 |
| 2010/0303321 A1* | 12/2010 | McEwan | A61B 5/0536 382/131 |
| 2012/0043969 A1 | 2/2012 | Holder et al. | |
| 2012/0197371 A1 | 8/2012 | Neisz et al. | |
| 2013/0150940 A1* | 6/2013 | Wilson | A61B 5/6877 607/118 |
| 2013/0172718 A1* | 7/2013 | Choi | A61B 5/6822 600/378 |
| 2014/0066803 A1 | 3/2014 | Choi | |
| 2015/0005680 A1* | 1/2015 | Lipani | A61B 18/20 601/15 |
| 2015/0105686 A1 | 4/2015 | Vasan | |

OTHER PUBLICATIONS

Holder ("Impedance changes during evoked nervous activity in human subjects: implications for the application of applied potential tomography to imaging neuronal discharge", Clinical Physics and Physiological Measurements 10(3):267-274 (1989))) (Year: 1989).*

Elahi ("Acute Sciatic Neuritis following Lumbar Laminectomy", Hindawi Publishing Corporation, Case Reports in Medicine, vol. 2014, Article ID 404386) (Year: 2014).*

Aristovich et al. "A method for reconstructing tomographic images of evoked neural activity with electrical impedance tomography using intracranial planar arrays" *Physiological Measurement* 35:1095-1109 (2014).

Dowrick et al. "A Custom EIT System Based on Off-The-Shelf Equipment" *Proceedings of the 15th International Conference on Biomedical Applications of Electrical Impedance Tomography*, p. 17 (Apr. 24, 2014).

Famm et al. "A jump-start for electroceuticals" *Nature* 496:159-161 (2013).

Fouchard et al. "Modular architecture of a Multi-frequency Electrical Impedance Tomography system: design and implementation" *36th Annual International Conference of the IEEE Engineering in Medicine and Biology Society*, p. 6076-6079 ( 2014).

Holder "Impedance changes during evoked nervous activity in human subjects: implications for the application of applied potential tomography (APT) to imaging neuronal discharge" *Clinical Physics and Physiological Measurement* 10(3):267-274 (1989).

International Search Report and the Written Opinion of the International Searching Authority corresponding to International Patent Application No. PCT/GB2016/051092 ) (14 pages) (dated Jul. 18, 2016).

Liston et al. "A cable theory based biophysical model of resistance change in crab peripheral nerve and human cerebral cortex during neuronal depolarization: implications for electrical impedance tomography of fast activity in the brain" *Medical & Biological Engineering & Computing* 50(5):425-437 (2012).

Schuettler et al. "A Flexible 29 Channel Epicortical Electrode Array" *Proceedings of the 13th Annual Conference of the International Functional Electrical Stimulation Society*, p. 232-234 (2008).

Search Report under Section 17 corresponding to Application No. GB1506760.6 (2 pages) (dated Sep. 8, 2015).

Kao et al. "Distinguishability of inhomogeneities using planar electrode arrays and different patterns of applied excitation" *Physiological Measurement* 24:403-411 (2003).

Vauhkonen et al. "A Kalman Filter Approach to Track Fast Impedance Changes in Electrical Impedance Tomography" *IEEE Transactions on Biomedical Engineering* 45(4):486-493 (1998).

Zariffa et al. "Use of an Experimentally Derived Leadfield in the Peripheral Nerve Pathway Discrimination Problem" *IEEE Transactions of Neural Systems and Rehabilitation Engineering* 19(2):147-156 (2011).

* cited by examiner

DETECTING ACTIVITY IN PERIPHERAL NERVES

CROSS REFERENCE TO RELATED APPLICATIONS

This application is a 35 U.S.C. § 371 national stage application of PCT International Application No. PCT/GB2016/051092, filed on Apr. 20, 2016, which claims priority from Great Britain Patent Application No. 1509503.7, filed on Jun. 2, 2015, which claims priority from Great Britain Patent Application No. 1506760.6, filed on Apr. 21, 2015, the contents of which are incorporated herein by reference in their entireties. The above-referenced PCT International Application was published in the English language as International Publication No. WO 2016/170327 A1 on Oct. 27, 2016.

The present invention relates to methods and apparatus for detecting activity in a peripheral nerve of a human or animal subject.

INTRODUCTION

Electrical modulation, including stimulation and blocking, of particular peripheral nerves for treatment of diseases and other medical conditions is known, for example through electrical stimulation of the vagus nerve to treat conditions such as anxiety, obesity and heart conditions, and through modulation of the carotid-sinus and renal nerves to treat hypertension.

Monitoring electrical activity in peripheral nerves can also be desirable for a number of different purposes. For example, Famm et al., Nature Volume 496 page 161, 11 Apr. 2013 discusses development of "electroceuticals" in which individual nerve fibres may be targeted to treat particular conditions, and observes that researchers need to map disease-associated nerves and brain areas to identify the best points for intervention.

Current techniques for detecting and monitoring electrical activity in peripheral nerves include the use of sharp electrodes which are used to penetrate into the interior of the nerve, for example, to detect voltages at a particular location in the nerve cross section. However, the technique is invasive, potentially damaging, and the number of locations which can be simultaneously monitored is limited by the number of electrodes which can be used simultaneously. Electrodes external to the nerve can be used to monitor electrical activity within the nerve, but the degree of resolution within the nerve which can be achieved is rather limited.

The invention addresses problems and limitations with the associated prior art.

SUMMARY OF THE INVENTION

Autonomic nerves typically comprise many hundreds or thousands of nerve fibres with different functional activities. In smaller nerves near to end organs, the differences may be related to different receptor types and locations within a particular organ. In larger autonomic nerves there are bundles of nerve fibres which connect to particular organs. For example, the cervical vagus nerve in the neck connects to about ten different organs such as the heart and kidneys. Somatic nerves similarly contain nerve fibres, bundles of nerve fibres and other regions of the nerve which connect to different muscles, parts of muscles, and other locations in the subject.

An aim of the present invention is to help localize different areas of activity within nerves. Accordingly, the invention provides methods and apparatus for imaging a cross section of electrical activity within a peripheral nerve, using electrical impedance tomography (EIT). With respect to the use of penetrating electrodes for direct measurement of nerve fibre activity, the invention can provide images of nerve activity over the whole cross section of the nerve. Devices according to the invention are suitable for long-term implantation, and so can be left in situ in human subjects.

With respect to the use of inverse source modeling to measure localised activity within nerves, the use of electrical impedance tomography provides an inverse solution (the image reconstruction) which is in principle unique, unlike inverse source modeling. In EIT, many more independent measurements are made from the same number of electrodes, for example with probe current being applied to a large number of different electrode pairs and a resulting voltage being collected from a large number of pairs of other electrodes for each probe current pair. Using EIT, the signal to noise ratio can also be improved using an impedance carrier AC probe current and a lock-in amplifier.

The invention may be applied to a variety of peripheral nerves including somatic nerves, and autonomic nerves such as the vagus and sciatic nerves.

More particularly, the invention provides a method of determining electrical properties in a peripheral nerve of a human or animal subject, comprising: spacing a plurality of electrodes around a perimeter of the peripheral nerve; for each of a plurality of combinations of said electrodes, applying a probe electrical signal to the electrodes of said combination and measuring resulting electrical responses at one or more of said electrodes; and using the electrical responses to determine electrical properties of the peripheral nerve within the perimeter.

Each probe electrical signal is typically a current signal, and the resulting electrical responses are typically measured as voltages, so that impedance (or equivalently conductance) of the peripheral nerve is therefore determined. Following suitable processing of the resulting electrical responses, for example including demodulation from a carrier frequency, demultiplexing where appropriate, and so forth, an electrical impedance tomography image reconstruction may be used to determine the electrical properties at one or more locations within the perimeter of the nerve. However, other mapping, pattern matching and similar techniques may be used to derive useful measures of electrical activity within the nerve if required, without going through a formal EIT reconstruction process.

The mechanism of resistance change during fast neural activity is thought to be ion channels opening so that current enters the intracellular space. As the AC frequency of the probe electrical signals increases, the applied current tends to be short-circuited by the membrane capacitance so that the impedance change decreases. However, it is unclear from the prior art what frequency ranges might be appropriate for carrying out EIT on peripheral nerves. Contributory noise effects might be found in components of the evoked compound action potential present in the carrier bandpass, and 1/f general physiological and electronic noise. The inventors have therefore used experimentation to judge what frequency ranges give improved performance for example in terms of signal to noise ratio. To this end, the probe electrical signals preferably have a frequency in the range 1 kHz to 20 kHz, the range preferably including the end values.

More specifically, the probe electrical signals preferably have a frequency in the range 5 kHz to 12 kHz, in the range 4 kHz to 8 kHz, in the range 5 kHz to 7 kHz, or in the range 9 kHz to 11 kHz, in each case the range preferably being inclusive of the specified end values. Probe electrical signals in these particular frequency ranges, and more generally in the range 1 to 20 kHz have been found by the inventors to be advantageous in providing improved signal to noise ratios in the resulting electrical responses and therefore in the determined electrical properties. These experimental results and ranges are particularly applicable to the myelinated axons contained within the peripheral nerve. For non-myelinated axons, the inventors have determined that probe electrical signals with a frequency in the range 1 kHz to 2 kHz, and/or in the range 4 kHz to 5 kHz, and more generally in the range 1 to 20 kHz are particularly advantageous, for example in providing reduced signal to noise ratios.

Probe electrical signals in these frequency ranges may be applied to one, some or all of the combinations of electrodes. The probe electrical signals may typically be narrowband sinusoidal signals in which substantially all of each such signal, or a majority of each such signal, in terms of amplitude, power or another suitable measure, is found at a frequency within the specified range, or at a range of frequencies within the specified range.

It should also be understood that these frequency ranges may refer as well or instead to frequencies or frequency bands of the resulting electrical responses detected or measured in respect of some or all of the combinations of electrodes.

Even where a tomography reconstruction process is used, and also where other analysis techniques are used, the determined electrical properties may be in the form of an image or map of a cross section of the nerve, or may be in respect of particular locations, or particular sub regions of the cross section, for example in particular geometrically defined areas, particular fascicles, or in particular locations or areas previously identified using the invention as relevant to particular activity in the subject.

Multiplexing schemes may be used in which probe electrical signals are simultaneously applied to each of a plurality of combinations of electrodes, and said electrical responses resulting from each of said plurality of combinations are simultaneously measured. Multiplexing could for example be carried out using a different carrier frequency or different code for each simultaneous combination of electrodes, and enables the nerve to be monitored at a faster rate, for example in order to better resolve action potential activity on time scales of a few microseconds to a few tens of microseconds.

In order to carry out electrical impedance tomography on peripheral nerves, the plurality of electrodes may be provided on a flexible cuff which is wrapped around the perimeter of the nerve so that the electrodes are in contact with the perimeter of the peripheral nerve. Some or all of the electrodes may be elongate along an axis of the peripheral nerve, and this can provide increased contact area, lower electrode contact impedance, and improved signal to noise ratio especially given the small size of the nerves to be monitored. The flexible cuff may be secured around the peripheral nerve using a clamp. The claim may be provided with a slot, and electrical connectors to the electrodes may then extend through the slot towards a connector for interfacing with the electrodes and/or a control unit connected to the electrodes.

Having determined particular electrical properties of the peripheral nerve being monitored, the method may further comprise applying one or more modulation signals to the same peripheral nerve, to modulate electrical activity of the peripheral nerve, for example for therapeutic purposes, or similarly such modulation of another nerve may be carried out dependent upon the determined electrical properties. In particular, the modulation signals may be generated dependent upon nerve activity determined at one or more particular regions of segments of the peripheral nerve.

One or more modulation signals to modulate electrical activity of a peripheral nerve may be applied to the nerve using some or all of the electrodes already described herein for the purposes of monitoring the same peripheral nerve, and this technique for nerve modulation may be used whether or not the electrodes are also used for detecting electrical activity in the nerve as discussed herein. In particular, selected or controlled combinations of modulation signals applied to all or a selected plurality of the electrodes may be used to provide a controlled or predetermined spatial profile of current (the profile being in terms, for example, of one or more of current magnitude, direction, frequency etc.) within the peripheral nerve, within the perimeter around which the electrodes are spaced. This controlled spatial profile may be constant or varied over time, and the total or localised currents induced within the nerve may also be constant or varying over time. In this way, selective and localised modulation effects may be provided to particular parts of the nerve cross section, for example in order to deliver therapeutic benefits. Such modulation may include selective stimulation, blocking and other influences and controls on nerve electrical activity, focused on desired parts of the cross section of the nerve, for example on such parts as identified using the present invention.

In order to map particular functions of the subject onto the cross section of the peripheral nerve, the method may comprise providing a signal representing a subject activity of the human or animal subject associated with electrical activity in the peripheral nerve; determining, during the subject activity, electrical properties within the peripheral nerve using the steps of any preceding claim; and comparing the signal representing the subject activity with the determined electrical properties to thereby identify one or more parts of the peripheral nerve within the perimeter which are associated with the subject activity.

For example, the subject activity may comprise providing stimulation at one or more locations of the human or animal subject which are remote from the plurality of electrodes, to thereby determine one or more parts of the peripheral nerve within the perimeter which are associated with the one or more locations. More generally, the subject activity may comprise autonomic or somatic activity of the human or animal subject, for example breathing activity, heart activity, and so forth. One or more modulation signals to thereby modulate activity of the peripheral nerve, optionally using the described electrodes to create a desired spatial/temporal profile of current within the cross section of the nerve as discussed above, may then be applied specifically to one or more of said identified parts of the peripheral nerve dependent upon the determined electrical properties.

The invention also provides apparatus for putting the above methods in to effect, including apparatus for monitoring a peripheral nerve of a human or animal subject comprising: a plurality of electrodes spaced arranged for contacting the peripheral nerve around the perimeter; and electrical connections to the electrodes for applying, to each of a plurality of combinations of the electrodes, a corresponding probe electrical signal, and for measuring, for each such combination of the electrodes, resulting electrical responses at one or more of said electrodes.

In particular, the electrodes may be disposed, for example in an array such as a linear array, on a flexible substrate arranged for wrapping around at least part of a perimeter of a peripheral nerve. The electrodes may be formed by apertures through a surface layer of the substrate, and the electrical connections are embedded within the flexible substrate, so as to be insulated from surrounding tissues and each other. For example, the electrodes and electrical connections may comprise conductive foil such as a metal foil, each electrode and the corresponding electrical connection being formed from a single piece of such conductive foil.

Some or all of the electrodes may be elongate in a direction along the axis of the peripheral nerve around which the substrate is arranged to be wrapped, and the apparatus may comprise at least 15 said electrodes; at least 30 said electrodes; or at least 60 said electrodes, in order to provide required electrical impedance tomography performance. The electrodes may be spaced at intervals appropriate to achieve the required number of electrodes for use with a particular diameter of nerve, but typically may be spaced at intervals of 3 mm or less; and in some case at intervals 0.3 mm or less.

The apparatus may comprise a signal source arranged to apply a corresponding probe electrical signal to each of said combinations of electrodes. So as to provide a reading of electrical properties of the nerve without interfering with nerve activity, the signal source may be arranged such that the applied probe electrical signals do not cause action potentials to be produced within the peripheral nerve, and/or do not significantly alter the shape of the compound action potential or its component elements.

In order to provide improved signal to noise ratio in the measured electrical responses, the signal source is preferably arranged to apply a probe electrical signal having a frequency in the range 1 kHz to 20 kHz, in the range 5 kHz to 12 kHz, in the range 4 kHz to 8 kHz, or in the range 5 kHz to 7 kHz, to one or more of said combinations of electrodes, including optionally to all of said combinations. Each such probe electrical signal may typically be in the form of an AC sinusoidal signal or signal components at a single such frequency within the specified range of frequencies. Alternatively or additionally, the specified frequencies and/or frequency bands may specify the frequencies of detection or measurement of the resulting electrical responses.

In order to determine and localise electrical properties within the nerve, the apparatus may also comprise a reconstructor function or element to receive signals corresponding to said electrical responses and to determine therefrom, by electrical impedance tomography image reconstruction, and/or by one or more other techniques, electrical properties at one or more locations within the peripheral nerve.

The apparatus may also comprise a modulator arranged to apply one or more electrical modulation signals to the peripheral nerve being monitored or in one or more other nerves, in order to modulate electrical activity in said nerve. The electrical modulation signals may be dependent upon the determined electrical properties, for example in terms of the position(s) on or in the nerve(s) to which the signal is applied, and in terms of the structure for example the timing and profile of current and/or voltage of the signal to be applied. The modulator may be arranged to impose a predetermined or desired spatial profile of current within the nerve using the electrodes as already mentioned above. The invention also provides apparatus for modulating a peripheral nerve comprising a plurality of electrodes (which may correspond to the electrodes described herein) spaced around a perimeter of the nerve, which are provided with controlled modulation signals so as to impose a predetermined or desired current profile within the cross section of the nerve which is surrounded by the electrodes.

All or part of the various apparatus discussed above and described in more detail below may be adapted for implantation in the human or animal subject. For example, the electrodes along with suitable conductors for electrical connection and a substrate supporting the electrodes need to be implanted in the subject, but one, more, or all of the other functions of the apparatus may also be arranged for implantation. Other functions of the apparatus not for implantation, as desired, may then be provided external to the human or animal subject and suitably connected to implanted elements via suitable wireless or wired connections.

For example, in some embodiments, both the signal source and reconstructor are provided as part of an implantable device which includes the electrodes, and which may also include for example a modulator function as set out above.

BRIEF DESCRIPTION OF THE DRAWINGS

Embodiments of the invention will now be described, by way of example only, with reference to the drawings, of which.

DETAILED DESCRIPTION OF EMBODIMENTS

Figure 1A:
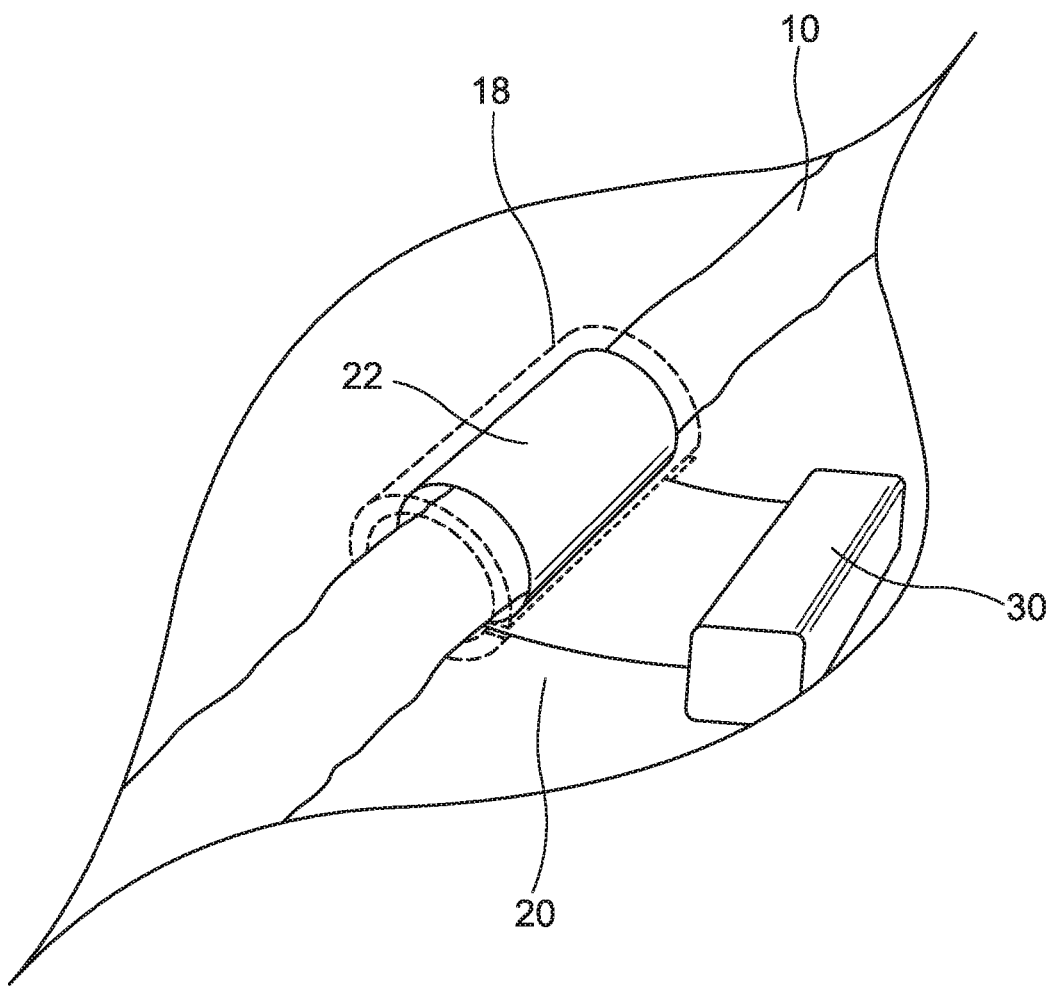
FIGS. 1A and 1B illustrate, in use, a device for monitoring a peripheral nerve of a human or animal subject.
Figure 1B:
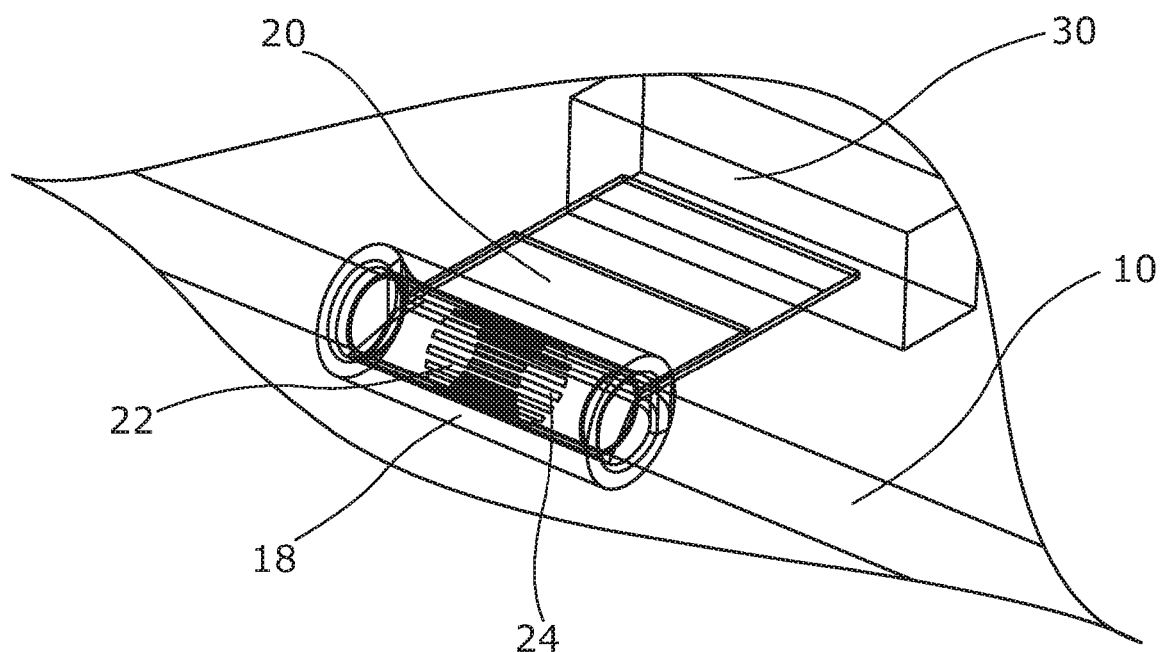

Referring to FIGS. 1A and 1B there are shown in different perspective views a peripheral nerve 10 of a human or animal subject, to which a nerve monitoring device 20 has been coupled. The nerve monitoring device is arranged to use electrical impedance tomography to detect electrical activity within the nerve, through changes in the electrical properties within the nerve, in particular to detect such activity at one or more locations within a cross section of the nerve at the location of the device. In particular, an image or map of such electrical properties over a cross section through the nerve may be derived, and the electrical properties may in particular be impedance.

Embodiments of the invention may operate at least in part by measuring the change in resistance produced by the opening of ion channels in the membranes of peripheral nerves as they fire. Probe current applied to the nerve using an externally applied probe electrical signal travels in the extracellular space of the nerve when a nerve fibre is at rest, because in this state nerve fibre membranes have a very high resistance. As ion channels open during the action potential of a nerve fibre, the externally applied probe current travels into the intracellular compartment of the fibre which contains additional conducting ions. This lowers the resistance of the bulk tissue by about 1% at DC, and typically less with increasing frequency of the applied current. Other mechanisms may also be effective in changing the apparent impedance or other electrical properties within the peripheral nerve which are evident from or can be derived from the electrical responses at the surface of the nerve to an applied electrical signal.

In FIGS. 1A and 1B the nerve 10 is shown as surgically exposed, but the device 20 may typically be surgically implanted in a permanent or temporary manner. The device 20 comprises a cuff 22 which wraps around an outside perimeter of the nerve 10 and which is provided with a plurality of electrodes 24 for contacting the nerve, without needing to penetrate into the nerve tissue, although some degree of penetration may occur, for example due to pressure exerted by the cuff, or be desirable, for example to reduce contact impedance. In FIGS. 1A and 1B the device also comprises an associated control unit 30 coupled to and located proximal to the cuff. Control functionality to support use of the cuff 22 and the electrodes 24 may be provided solely within the control unit 30, or partly or solely in one or more other units located within and/or external to the subject, for example in external electronics and person computer equipment, or in a mixture of these options.

The cuff 22 may be held in place around the nerve in a variety of ways. In FIGS. 1A and 1B a clamp in the form of an elastomeric tube 18 having a slot allowing a portion of the cuff to extend away from the nerve towards the control unit 30 has been used. The clamp then holds an interior surface of the cuff, on which the electrodes are exposed, against the periphery of the nerve. More generally, the clamp may be designed in a way that it holds the array, which is wrapped around the nerve on the side proximal to the control unit, holding and pressing both tails of the array against each other. The clamp is designed in a way that the force, applied to the nerve from the cuff, is limited so it is impossible to damage the nerve during normal operation.

Figure 2:
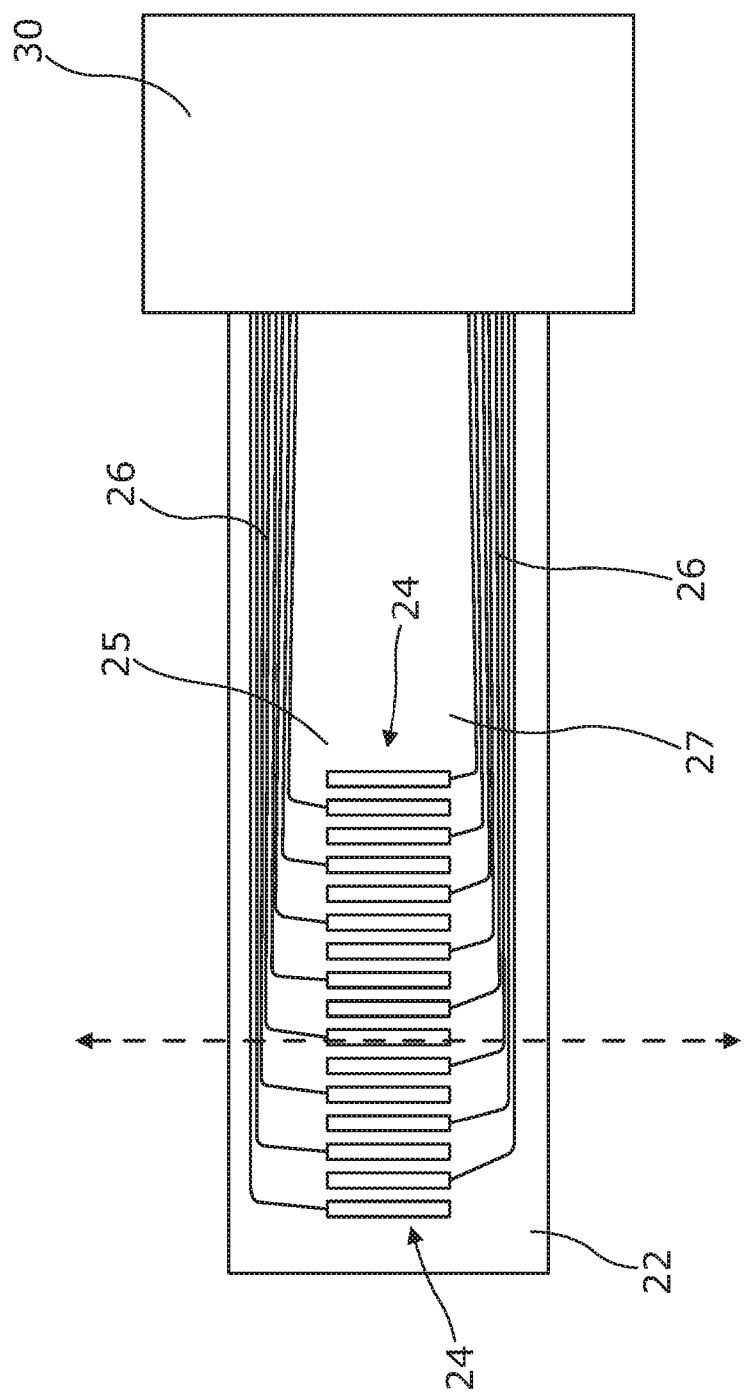
FIG. 2 shows the device of FIGS. 1A and 1B in an open configuration before use.

The nerve monitoring device 20 is shown in FIG. 2 in an open configuration, before being coupled to a nerve. However, for clarity the general alignment of a nerve about which the cuff may be wrapped is shown as a dashed axis. The cuff is provided by disposing the electrodes 24 on an interior surface 25 of a flexible substrate 27 comprising an elastomeric or similar material. When the interior surface of the substrate 27 is wrapped around the nerve, the electrodes then form an array distributed around a perimeter of the nerve.

Typically, the electrodes 24 may be extended or elongate in the direction of the axis of the nerve. Electrical connectors 26 are provided on the cuff, typically embedded within the flexible substrate 27 so as to be insulated from surrounding body fluids and tissues, and from each other and the electrodes, and are arranged to electrically couple each electrode 24 to the control unit 30, or at least to suitable connection pads or similar at a distal end of the substrate, for onward connection. The substrate 27 of the cuff is generally planar and formed of an elastomeric and/or flexible material, so that it can easily be wrapped around the nerve as described.

The electrodes 24 and/or the connectors may be formed using a variety of different conducting materials. Conveniently, metal foil may be used, for example of stainless steel, platinum or gold, and an electrode and the corresponding connector may be formed from a single such piece of foil or other conductive material. However, other conductive materials such as carbon (for example in the form of carbon nanotubes) may be used, and materials may be deposited in various ways such as by sputtering and vapour deposition.

Typically, the electrical conductors will be insulated using one or more insulator layers, preferably also of an elastomeric material, and the electrodes may be formed by exposing conductive material, for example the above mentioned metal foil or another conductor layer, through apertures in these one or more layers. Therefore, although the electrodes of FIG. 2 are shown generally as rectangles, these rectangles could equally represent areas of conductor which are covered by an insulator, with the electrodes being formed by apertures through the insulator to expose portions of the areas of conductor.

For convenience of illustration, an array of only sixteen electrodes 24 is shown in FIG. 2. However, the number of electrodes 24 for disposing around the peripheral nerve may vary, typically being at least 15, and optionally at least 30 or at least 60. The cuff 22 and the associated electrodes 24 may be of a size and configuration suitable for wrapping around a particular peripheral nerve, for example around such a nerve having a specific diameter or a range of diameters of around 0.5-3.0 mm. For example, in human subjects typical nerve diameters may be 2-5 mm for vagus nerve, or 0.5-3 mm for the isolated branches of the peripheral nervous system. To this end the length of the array of electrodes 24 may typically be in the range of about 1.5 mm-15 mm, which is short enough for the majority of the nerves of the human and small mammalian nervous systems.

An array of electrodes which is longer than required to contact around the entire perimeter of a particular nerve may still be used for that nerve by not using one or more of the electrodes at one or both ends of the array, thereby making the effective length of the array shorter. Some particular ways in which the cuff and the associated electrodes and electrical connectors may be formed are discussed in more detail later in this document.

The electrodes may be spaced on the surface of the cuff at an interval which is suitable for providing sufficient electrodes around the perimeter of a nerve to enable a suitable electrical impedance tomography reconstruction to be carried out. For typical nerve sizes, a variety of such spacing intervals may be used, but these will typically be 3 mm or less, or 0.3 mm or less, and optionally less than 0.05 mm for smaller nerves. The widths of the electrodes to accommodate these spacings while still providing sufficient isolation between the electrodes may typically be around 20% to 50% of the spacing. For example, for use on a human sciatic nerve the spacing interval could be as much as 3 mm, whereas for 256 electrodes around a very small autonomic nerve the spacing could be down to about 3 µm, although more likely in the range 0.2 mm down to about 20 µm.

Figure 3:
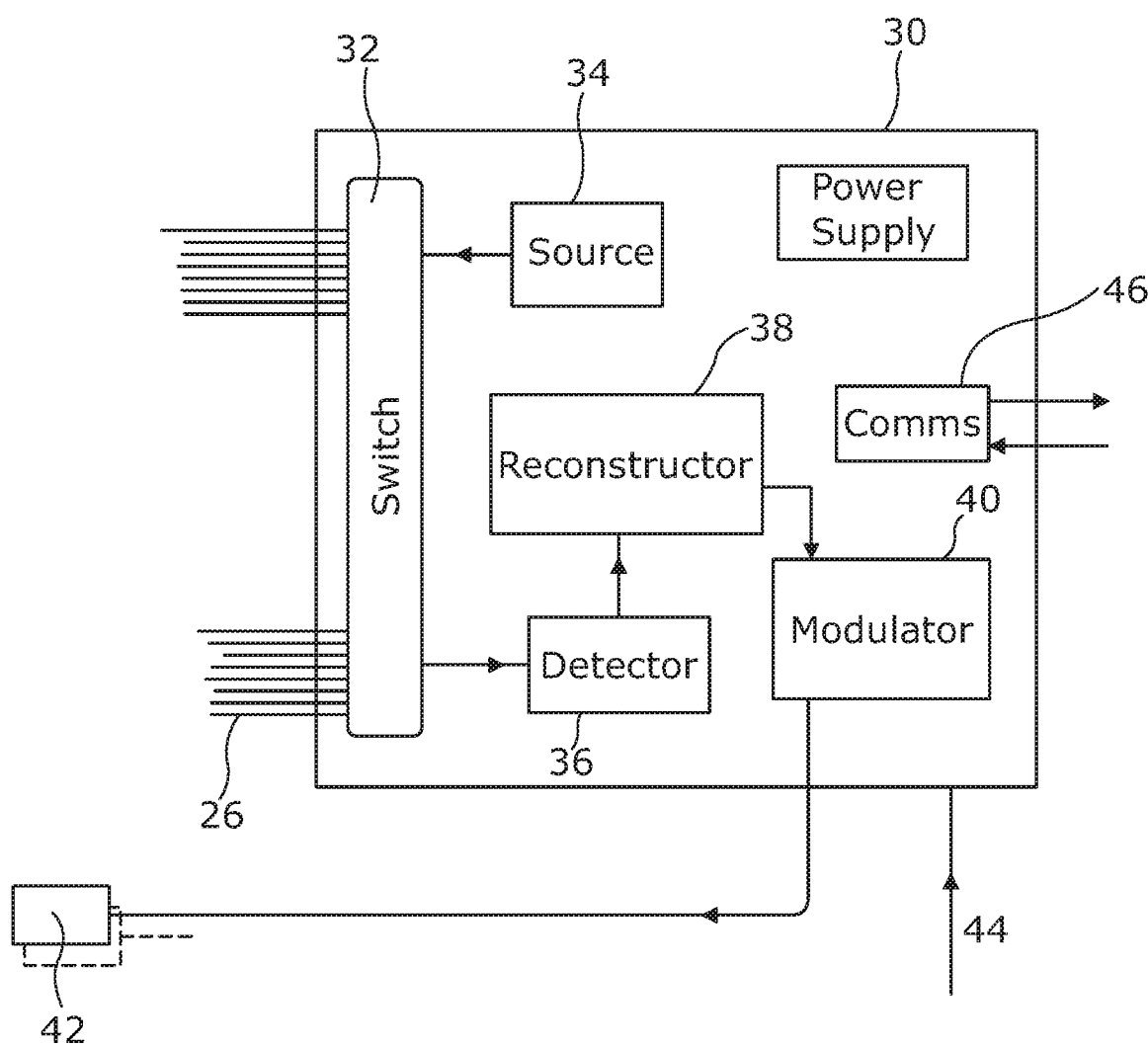
FIG. 3 illustrates schematically function elements which may be provided in the controller of FIG. 30, and/or elsewhere including external to the subject, in order to carry out the invention.

Aspects of the control unit 30 are shown schematically in FIG. 3. The electrical connections 26 embedded within the substrate 27 of the cuff 22 are coupled to a switch 32 which allows particular electrodes or combinations of electrodes 24 to be selected and coupled to other parts of the control unit 30. A signal source 34 can then be connected across any such combination of electrodes 24 in order to apply a probe electrical signal to or between the electrodes of the combination. A detector 36 is then used to measure resulting electrical responses at one or more of the electrodes, again as connected to the detector by the switch 32. Techniques of providing probe electrical signals and collecting and processing the resulting electrical responses to generate a tomographic image or other data relating to electrical properties within the space surrounded by the electrodes are set out in WO2009/068961 and WO2010/128326, the contents of which are incorporated herein in their entirety for all purposes.

Typically, the signal source 34 provides an alternating current probe signal across a particular pair of electrodes 24, and the detector 36 may then detect a corresponding alternating voltage at each of a plurality (some or all) of the other electrodes 24 which are in contact with the nerve. The measured voltages, taken in combination for the signal source being applied to many different pairs of electrodes, then allows an impedance or conductance map within the ring of electrodes to be deduced. The probe signal may be AC or DC, although in practice AC is nearly always used. The probe signal is usually a current signal, so that the measured resulting electrical responses are voltages, but the probe signal may be a voltage signal and the resulting electrical responses are then currents. In either case, the resulting electrical response represents a measure of impedance due to the peripheral nerve. In some cases, the phase of the probe signal is varied. This allows for a pair of phase/antiphase segments to be added or subtracted, thus revealing any intrinsic voltage signal not arising from the probe signal, or to remove such intrinsic voltages. Such paired subtraction techniques are described for example in WO2010/128326.

Although a probe electrical signal may be applied to each combination of electrodes in turn, with electrical responses then being recorded for all relevant electrodes before a probe signal is applied to the next combination of electrodes, multiple combinations of electrodes may be probed in parallel using multiplexing techniques. Some such techniques are discussed in WO2009/068961, including techniques using frequency division and code division multiplexing between multiple different combinations of electrodes. Use of such multiplexing allows a complete set of resulting electrical responses to be collected very rapidly, commensurate with the short time scales of the duration of action potentials, typically a few milliseconds, in peripheral nerves.

As discussed towards the end of this document with reference to FIG. 8, the inventors have found that for electrical impendence tomography of peripheral nerves, an improved signal to noise ratio can be obtained when the probe electrical signals have a frequency in the range 5 kHz to 12 kHz, in the range 4 kHz to 8 kHz, or more particularly in the range 5 kHz to 7 kHz. Such applied frequencies may be defined in terms of one or more narrow band frequencies, or frequency components of the signals applied to the electrodes, in terms of particular frequencies or frequency bands of the applied signals being detected in the resulting electrical responses, or a combination of the two.

Probe electrical signals in these frequency ranges may be applied to one, some or all of the combinations of electrodes. The probe electrical signals may typically be narrowband sinusoidal signals in which substantially all of each such signal, or a majority of each such signal, in terms of amplitude, power or another suitable measure, is found at a frequency within the specified range, or at a range of frequencies within the specified range.

Probe signals falling within other ranges of frequency also provide advantages in terms of signal to noise ratio and/or other aspects of electrical impendence tomography of peripheral nerves, including the range of 1 kHz to 20 kHz.

The probe electrical signal should preferably give rise to currents within the peripheral nerve which do not cause action potentials to be produced or significantly alter the shape of the compound action potential or its component elements. In other words, the probe signal should not significantly alter behaviour of the monitored peripheral nerve. The limit on such currents within the nerve so as not to affect nerve behaviour may depend on frequency of the probe signal.

In particular, the monitoring device 20 may be used to measure transfer impedances using a four electrode method. The probe electrical signal is then applied to two of the electrodes, and the resulting electrical responses are measured between each of a plurality of different pairs of other electrodes. These pairs may be measured one by one in series, or together at the same time in parallel, or in other ways. Using a four electrode method and transfer impedances avoids having to take into account the contact impedances of the electrodes delivering the probe electrical signals. Of course, more than two electrodes can be used to apply the probe signal, for example combinations of larger numbers of electrodes in a desired spatial pattern. The measured electrical responses as signals of AC (or sometimes DC) voltage or current then correspond to transfer impedances, and comprise the carrier frequency of the probe signal modulated over time by changes in impedance in the peripheral nerve. The voltages or currents of the electrical responses are therefore converted to impedance signals by demodulation with respect to the carrier frequency of the applied AC signal to give a complex impedance which varies over time. Different aspects of this complex impedance may be used to derive the required electrical properties of the nerve. Usually, the real components of the measured transfer impedances are used, because this is least contaminated by stray capacitance. However, any property of the complex impedance such as phase angle, modulus, or quadrature component may be used. Electrical properties of the peripheral nerve determined from the measured electrical responses may be generated in an absolute form, or more usually at a difference over time or applied frequency.

The control unit 30 may therefore also comprise a reconstructor 38 which is arranged to carry out an electrical impedance tomography reconstruction of the resulting electrical responses, to thereby derive corresponding electrical properties, typically corresponding to impedance, at a plurality of locations within the cross section of the nerve around which the array of electrodes is disposed. These derived electrical properties of the nerve then correspond to nerve activity at the plurality of locations, for example as demonstrated by the examples below. The reconstructor 38 may be arranged to provide a map or image of the electrical properties across the cross section of the nerve, or may be arranged to provide the electrical properties at one or more selected points or in one or more selected regions of the nerve cross section. Also, instead of being provided as part of the control unit, tomographic reconstruction may be provided by an external entity separate to the control unit 30. The resulting data may demonstrate nerve activity at various levels of resolution, for example in particular geometric parts, particular fascicles, other groups of nerve fibres, and even in particular nerve fibres.

Although the reconstructor 38 may be used to generate an electrical impedance tomography map or image in cross section through the nerve, the measured electrical responses may be used in other ways. For example, a mapping technique may be used in which information from the responses is used more directly, as a map onto the surface of the peripheral nerve. In other examples, machine learning, and other classifier and statistical techniques may be used to identify patterns of activity within the nerve without requiring reconstruction of a tomographic image. These examples may provide useful results from the electrical responses more quickly than is possible using a full tomographic image reconstruction.

The control unit may also comprise a modulator 40 which is arranged to apply a modulation signal to the peripheral nerve 10 to modulate activity within the nerve, the modulation signal being generated and applied dependent upon the detected electrical properties or activity of the nerve at one or more locations or in one or more regions as determined by the reconstructor 38. This modulation signal could for example be applied to the nerve using one or more of the electrodes 24, or using one or more additional electrodes 42, or in some other way. The modulation signal could be for providing stimulation, suppression, or a combination of such effects to the nerve or particular parts thereof, and could be applied to the same peripheral nerve 10 as that being monitored by the nerve monitoring device 20, or could be applied to a different nerve. The modulator 40 may also be arranged to generate the modulation signal for modulating nerve activity dependent upon another signal 44 input to the modulator, which could for example be detected activity of another nerve, optical, temperature, acceleration, pressure sensor, a signal dependent on glucose concentration or another chemical signal, or other electrical signal sensors.

The modulator may provide one or more modulation signals to modulate electrical activity of a peripheral nerve using some or all of the electrodes already described herein for the purposes of monitoring the same peripheral nerve, and this technique for nerve modulation may be used whether or not the electrodes are also used for detecting electrical activity in the nerve as discussed herein. In particular, selected or controlled combinations of modulation signals applied to all or a selected plurality of the electrodes may be used to provide a controlled or predetermined spatial profile of current (the profile being in terms, for example, of one or more of current magnitude, direction, frequency etc.) within the peripheral nerve, within the perimeter around which the electrodes are spaced. This controlled spatial profile may be constant or varied over time, and the total or localised currents induced within the nerve may also be constant or varying over time. In this way, selective and localised modulation effects may be provided to particular parts of the nerve cross section, for example in order to deliver therapeutic benefits. Such modulation may include selective stimulation, blocking and other influences and controls on nerve electrical activity, focused on desired parts of the cross section of the nerve, for example on such parts of the nerve as identified using the present invention.

The control unit 30 may also comprise a power supply 46, for supplying power to the other elements of the control unit described herein, for example using a battery or similar. As already mentioned, one or more functions of the control unit 30 may instead or additionally be provided in an additional unit located proximal to or distal from the device 20, inside or outside the human or animal body in which the device is implemented.

Aspects of the control unit 30 and related functionality described herein may be implemented using one or more microprocessors with associated memory for storing programs and data. For example, the functionality of the reconstructor 38 to carry out the electrical impedance tomography reconstruction may be carried out in software using such a microprocessor.

The control unit 30 may also be provided with a communications interface 44 for inputting and/or outputting data and/or control signals, for example using a wired or wireless link. Some uses of such a control unit include outputting determined electrical properties of the nerve being tested, for example as an electrical impedance tomography map or image.

The described apparatus may be used to identify one or more parts of the peripheral nerve which are associated with one or more particular locations of the human or animal subject, or associated with one or more activities such as an autonomic or somatic activity, or with one or more other functions such as heart, bladder and endocrine functions. Using the apparatus and methods described herein, electrical activity within the nerve, for example fast activity on the time scale of a few milliseconds, can be imaged with a resolution of about 10% of the nerve diameter. This electrical activity can then be correlated with known activity from a particular target organ to allow an anatomical map of the nerve fascicles or other regions of the nerve to be derived. This provides a major improvement in mapping regions of the cross section of the nerve to particular functions and activities which would otherwise require invasive and relatively crude penetrating electrodes to particular points within the nerve cross section to be used.

Once relevant aspects of mapping of the nerve cross section to activity and functionality is understood, understanding and monitoring functions and activities by monitoring the relevant parts of the nerve cross section using the same electrical impedance tomography or other techniques can be easily carried out, and the same or other nerves can be modulated in desired ways based on the data collected.

For example, implementations of the invention may provide an implantable device having a cuff as described with around 32-64 electrodes, and appropriate functionality in the control unit to provide electrical impedance tomography maps or other data at various rates as required, for example at about 1 kHz. Such a device may be powered using a battery and operate using a microprocessor for control of the switch 32, signal source 34, detector 36, and implementation of the reconstructor function 38.

Apparatus implementing the invention may be used, for example, to treat or control asthma by stimulation of autonomic nerves to the lungs. Such stimulation would dilate the constricted bronchioles. It is surgically more practical to place an electrode cuff 22 around the vagus nerve in the neck, but this contains autonomic nerves to all of the abdominal organs such as the heart, bladder and bowel as well, and the present invention can therefore be used to identify those portions of the cross section of the nerve at the cuff which are functionally linked the required organs or other locations or functions in the subject. Surgical implant of devices at the vagus nerve in the neck is already routine, for example for stimulation in the treatment of epilepsy. Particular parts of the cross section of the nerve which are associated with a particular function or activity, such as the lungs, can be identified using the invention by seeing which parts of the cross section show electrical activity in correlation with the subjects breathing activity. Thus side effects from stimulation of parts of the nerve cross section associated with other organs may be minimised. In addition, intelligent analysis of the detected patterns of electrical activity may be used to fine tune modulation of the same and/or other nerves for maximum therapeutic effect.

Figure 4:
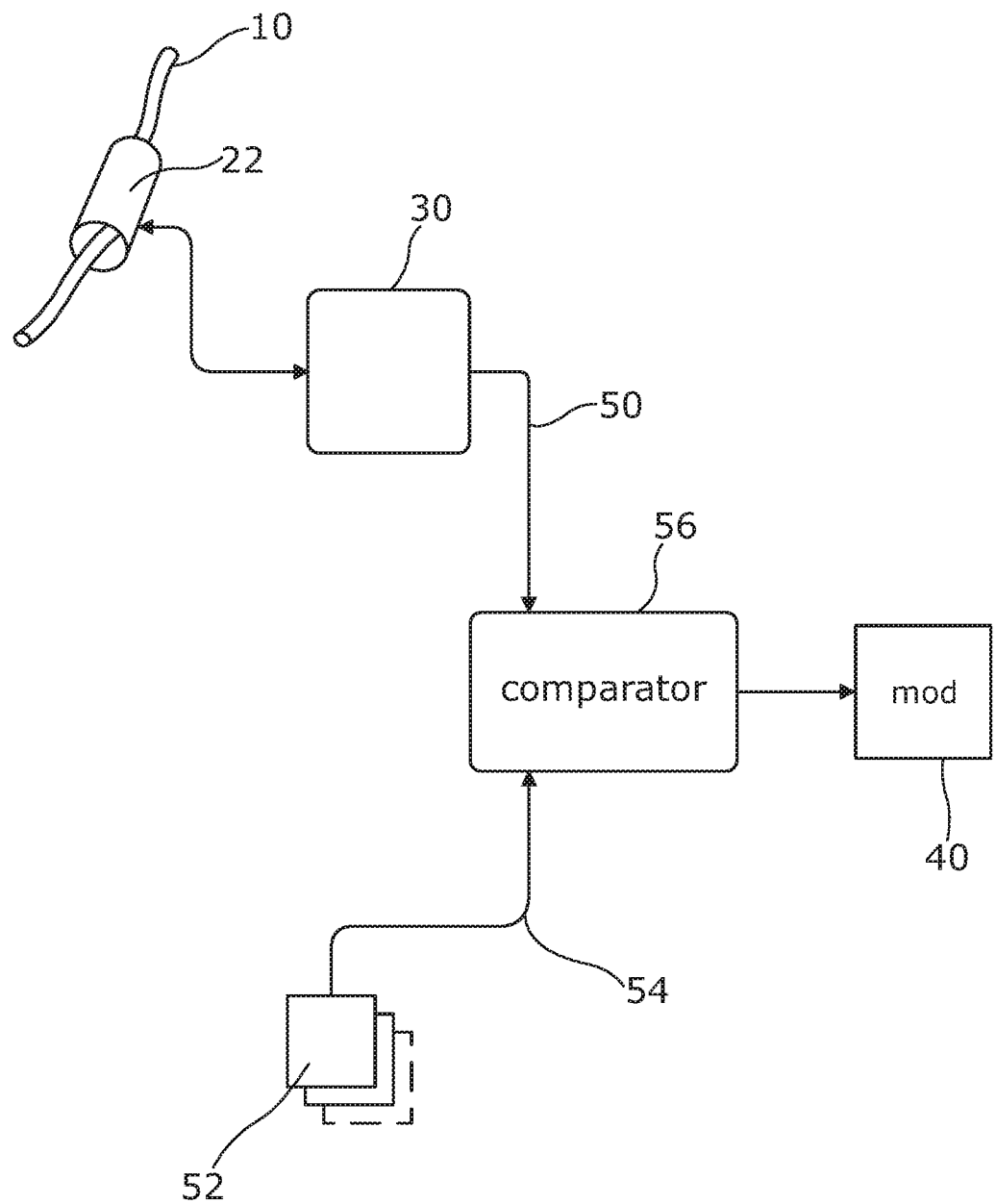
FIG. 4 shows how electrical properties of the peripheral nerve may be compared with other signals relating to activity in the subject in order to associate the subject activity with particular parts of the cross section of the peripheral nerve.

To this end, FIG. 4 illustrates apparatus according to the invention, including a cuff 22 carrying electrodes 24, coupled to a control unit to carry out electrical impedance tomography of a peripheral nerve 10 in a human or animal subject, to determine electrical properties at a plurality of particular locations within the nerve, for example as a tomographic map or image of the nerve cross section. The electrical impedance tomography (EIT) is carried our repeatedly to provide an EIT signal 50, at the same time as one or more further sensors 52 obtain one or more other signals 54 relating to activity or functionality of the human or animal subject which is expected to be associated with electrical activity in the nerve. Such further sensors could, for example, detect lung ventilation by measuring pressure and oxygen, heart beat using an electrical cardiogram, glucose concentration via a chemical sensor, bladder filling via a pressure sensor, muscle activation measured with an electrical or strain sensor, and so forth.

A comparator 56 is then used to compare or correlate at least some aspects of EIT signal 50 with at least some aspects of the other signals 54 in order to associate the activity or functionality with particular parts of the cross section of the nerve. As described elsewhere herein, the activity or functionality could be related to lung or heart function, or to stimulation or activation of or in a muscle or limb. If also required, a modulator 40 may then be used to provide a therapeutic or other effect to the subject on the basis of aspects of the EIT signal 50 which are determined to be associated with the targeted activity or functionality. The modulator 40 is already shown as optionally being comprised within the control unit 30 of FIG. 3. The comparator 56 of FIG. 4 may also be comprised within the control unit 30 in a similar way, with the further sensors 52 being suitably connected to the control unit 30 for example by electrical conductors.

Some example techniques which may be used to form the electrodes 24, the electrical connections 26, and the cuff 22 of FIG. 2 will now be described. In particular, the electrodes 24 may be constructed using sandwiched metal-on-silicone laser cutting. This general technique is discussed in Schuettler et al, 2008 (published online at http://ifess.org/proceedings/IFESS2008/IFESS2008_067_Schuettler.pdf), and comprises these steps:

1) Deposition of 0.1 mm thick silicone rubber onto stainless steel or platinum metal foil having a thickness of 10-50 µm;

2) Laser-cutting the geometric design required to form the electrodes and connections. Electrical contact surfaces within which the electrodes are to be formed may be rectangular, with dimensions of about 2 mm×80 µm. The electrical connections 26 and larger connection pads for attachment to the control unit are made from the same continuous foil. Typically, the electrodes 24 and connector pads then remain exposed but the electrical connections 26 are insulated by a second layer of silicone rubber.

3) Manual removal of unwanted foil areas using a binocular microscope and fine tweezers, 4) Deposition of another 0.1 mm silicone rubber layer, 5) Laser-cutting of electrical contact and connection pad apertures 6) Laser-cutting of the outline of the array of electrical connections and connection through-holes.

To make much smaller cuffs an approach using evaporation of a metal such as gold onto a film such as of polyimide may be used, to produce an array of gold metal electrodes on a polyamide film cuff.

The cuff and therefore the array of electrodes 24 should be flexible so that it can be wrapped around the nerve 10. It is desirable to have a design which provides many electrodes 24 around the nerve but allows for differing nerve diameters. The mechanical design provided herein can achieve this by providing more electrodes than are needed to make contact around the perimeter of a typical nerve on which the array is to be used. The array may then be wrapped around the nerve and surplus electrodes then form part of a sleeve; these are not used for monitoring the nerve.

To hold the cuff in place about the nerve, a second thicker silicone rubber incised cylinder, for example as illustrated as tube 18 in FIGS. 1A and 1B, may placed around the nerve and cuff to hold the cuff in place. This ensures good contact between the electrodes 24 and the nerve, minimises invasiveness of the installation procedure, and enclosed moisture around the nerve.

The silicone rubber should be biocompatible. The stainless steel of the electrodes may be platinized to produce a platinum black surface to reduce contact impedance. Instead of stainless steel, pure platinum could be used, or any bio-compatible metal alloy.

Some examples of specific implementations of the control unit 30, or equivalent functionality provided elsewhere in the apparatus, will now be provided. The signal source 34 may be provided by a constant current source which is able to accurately source small currents, for example in the range from about 1 µA to about 1 mA, up to an AC frequency of about 100 kHz, coupled to a very large output impedance (for example about $10^{14}$ Ohms) and excellent stability across variations in load, current magnitude and frequency, along with low noise. The detector 36 may comprise a multi-channel bio amplifier (for example a 128 channel amplifier) with 24 bit resolution and up to 100 kHz sampling rate per channel. For implementation as part of a control unit 30 for implantation with the cuff, some more specific constraints may assist with suitable miniaturisation, for example if signal from the required location is high the following parameters are enough to satisfy reliability of event detection: current with 1-100 µA amplitude at DC—100 kHz, and bio-amplifier with 16 bit resolution with 30 kHz sampling rate.

The reconstructor may use a variety of known tomographic image reconstruction techniques. These include a 0-th order Tikhonov regularization with coefficient of variance correction. The procedure is described in Aristovich et al. 2014, published at http://iopscience.iop.org/0967-3334/35/6/1095/article. This does not include temporal information: instead each time point is reconstructed separately, and then they are combined into a sequence of images. This approach has been widely used in EIT image reconstruction.

Another technique which may be used for tomographic reconstruction is discussed in Vauhkonen M. et al., IEEE transactions on Biomedical Engineering, volume 45, issue 4 page 486, in which an algorithm for EIT reconstruction that is able to track fast changes in the impedance distribution is proposed, based on the formulation of EIT as a state-estimation problem and the recursive estimation of the state with the aid of a Kalman filter.

To demonstrate that impedance changes can be detected using a suitable arrangement according to the invention, and correspond to nerve activity, an 18 electrode cuff constructed using silicone rubber and stainless steel as discussed above was fitted to the sciatic nerve of an anesthetized rat, with 16 of the electrodes being used during the experiment. Repetitive electrical stimulation of a distal branch of the sciatic nerve at the hind paw was then carried out with pulses of 10 mA current and 1 ms duration every 100 ms, activating as many fibers as possible, and evoking a time dependent response in the sciatic nerve at the remote location of the cuff. Impedance recordings were performed using a probe signal of 50 µA current injection between opposite electrode pairs, with simultaneous measurements of resulting electrical responses of voltage being made at the remaining 14 electrodes. 100 stimulation evoked traces were averaged to produce impedance changes in measurement channels over time, as illustrated in FIG. 5.

Figure 5:
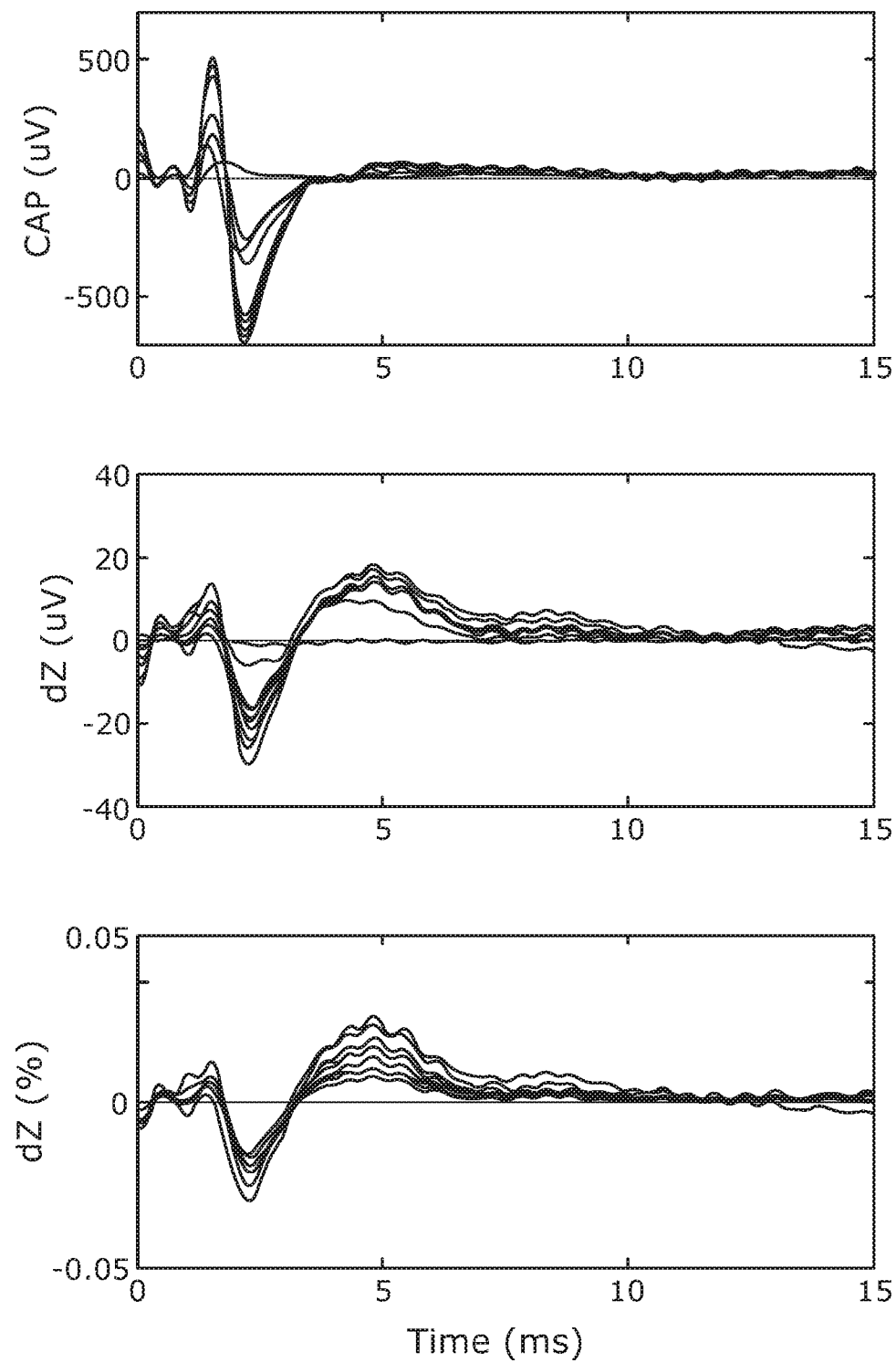
FIG. 5 shows compound action potential (upper plot), modulated transfer impedance change (middle plot) and normalised resistance change (lower plot) over time when a method according to the invention was carried out on an anesthetized rat along with repetitive stimulation of a distal branch of the sciatic nerve.

In particular, the upper of the three plots of FIG. 5 shows the compound action potential recorded at the cuff, that is the voltages recorded by a plurality of the electrodes which result from nerve activity, but absent any probe electrical signal. These action potential recordings therefore represent nerve signals compounded from the thousands of separate nerve fibres in the sciatic nerve as a result of the applied stimulation at the remote hind paw.

The middle plot of FIG. 5 shows the modulated transfer impedance change over time recorded from multiple combinations of four electrodes (two electrodes for the applied electrical signal current, and two electrodes to measure a differential voltage). Each curve represents a different electrode combination. By comparison with the top plot of FIG. 5, the curves in this plot therefore demonstrate that the electrical responses which can subsequently be used to carry out a tomographic reconstruction to determine properties at particular locations are indicative of nerve activity.

The lower plot of FIG. 5 represents the normalised resistance change over time in %, which corresponds to the data of the middle plot.

Figure 6:
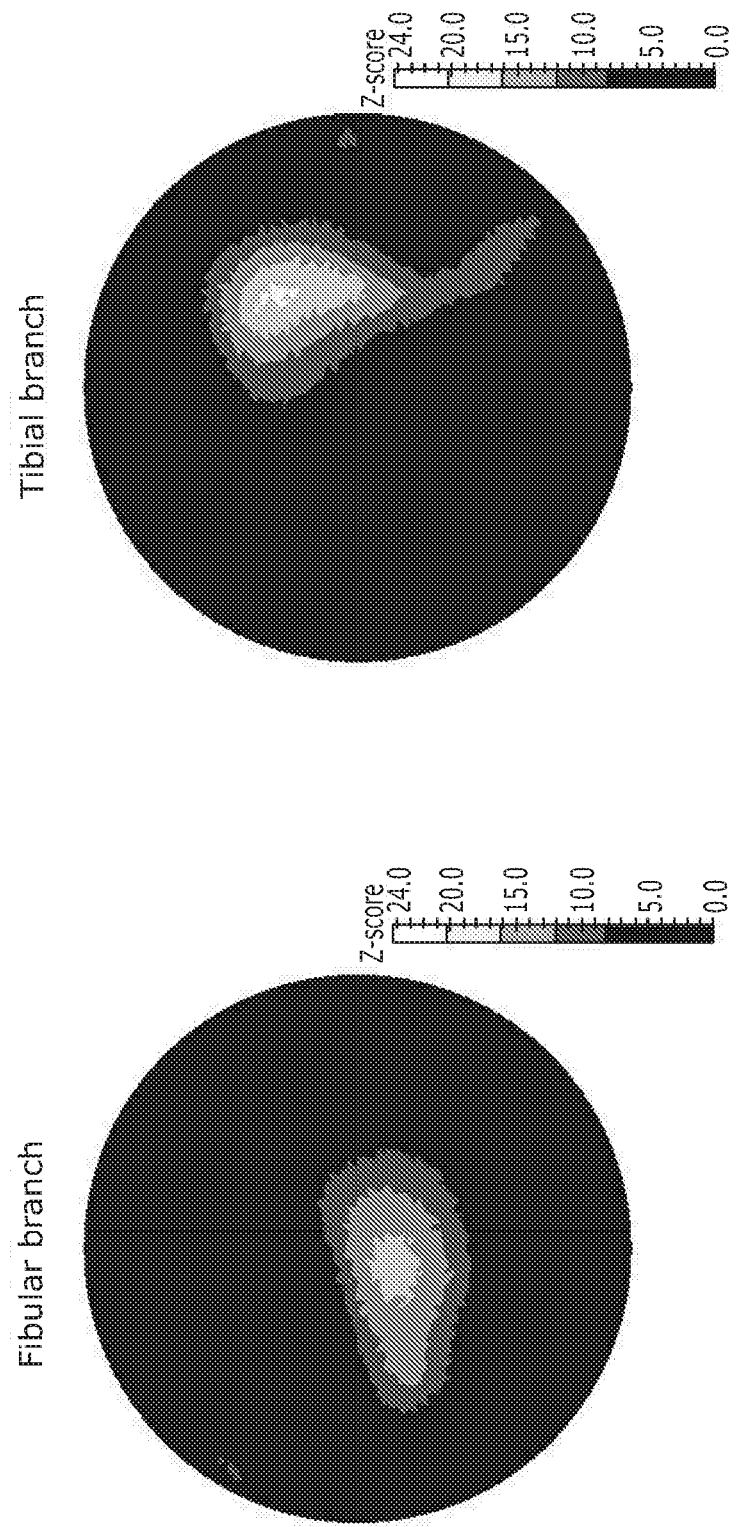
FIG. 6 shows electrical impedance tomography images of the sciatic nerve of a rat. The left hand and right hand images show nerve activity resulting from electrical stimulation of the fibular branch and tibial branch respectively.

To demonstrate that electrical impedance tomography can be used according to the invention to identify portions of the cross section of a peripheral nerve which correspond to particular functionality of the subject, the invention was used to image fast neural activity in the sciatic nerve of a rat, along the lines already discussed in connection with FIG. 5 above, but continuing to actually form an image of nerve activity based on electrical impedance tomography and using a longer stimulus interval of 200 ms. The results are illustrated in FIG. 6. In the figure, the left hand image represents sciatic nerve activity detected as a result of electrical stimulation in the fibular branch, and the right hand image as a result of electrical stimulation in the tibial branch.

Each electrical impedance tomography image was reconstructed from a single set of impedance measurements comprising an average of 50 consecutive impedance recordings. In each of these recordings a constant current of between 5 and 70 µA at an AC frequency of between 0.1 and 100 kHz was injected through a pair of electrodes spaced around 157.5° apart (e.g. electrodes 1 and 14 in a ring of 16 evenly spaced electrodes), and voltages were recorded simultaneously on the remaining electrodes. This was then repeated for all electrodes in the ring. The resulting recorded voltages were then divided into trials, demodulated around the carrier frequency with a suitable bandwidth, and the trials averaged, resulting in impedance traces over time starting with the beginning of the stimulus. This yields 14 voltage measurements for each electrode pair used for current injection, so 14×16=224 transfer impedance measurements. For a 64-electrode array there will therefore be 62×64=3968 traces. These traces are then reconstructed into a sequence of cross-sectional images over time with a time resolution of 0.1 to 0.5 ms.

From the images, which each represent just one selected time frame, it can be seen that stimulation of the fibular and tibial branches gives rise to very different patterns of electrical properties.

Figure 7:
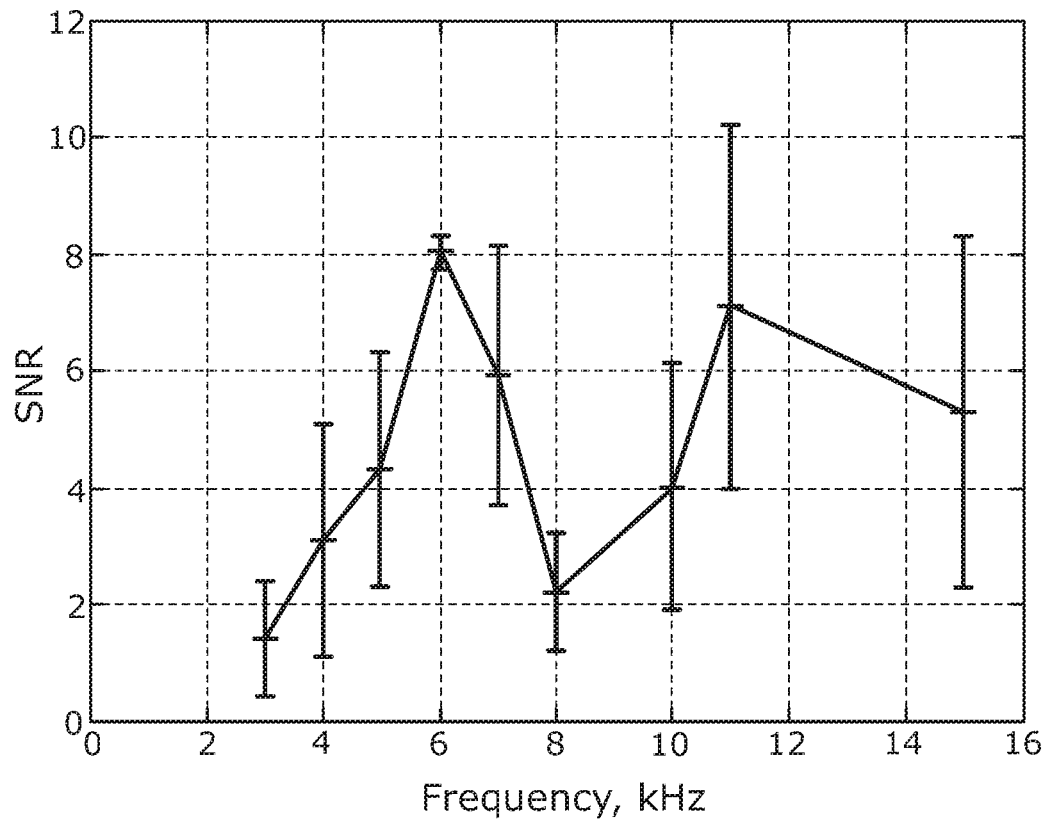
FIG. 7 shows a graph of signal to noise ratio found in carrying out electrical impedance tomography on the sciatic nerve of an animal model, at a range of different frequencies of the probe electrical signals.

Referring now to FIG. 7, experiments were carried out to determine the effectiveness of using probe electrical signals of different frequencies, in terms of signal to noise ratio and/or other benefits which may be found in the properties of the measured electrical responses and determined electrical properties of the peripheral nerve. In particular, an experiment similar to those already discussed above in respect of FIGS. 5 and 6 was carried out using 16 electrodes in a cuff disposed about a rat sciatic nerve. In any one recording step, an alternating probe current signal was injected through two electrodes which were one electrode step away from being diametrically opposed, and voltages were recorded from the remaining fourteen electrodes. In a subsequent recording step, the alternating probe current signal was applied to the next pair of electrodes in a rotation, and so on. There were therefore 16×14 transfer impedance recordings in any one data set, each transfer impedance recording being the average of 50 compound action potentials. All 234 such recordings were reviewed and the one with the largest transfer impedance change was selected. In this selected recording trace, the "signal" was then considered to be the peak impedance change and the noise is considered to be the peak-to-peak variation in the baseline trace, to thereby derive a measure of the signal to noise ratio.

The above steps were repeated using probe electrical signals at a variety of frequencies within the range 1 kHz to 20 kHz, in particular at 3, 4, 5, 6, 7, 8, 10, 11 and 15 kHz, with 30 recordings at 6 kHz, 5 recordings at each of 3, 4, 8 and 11 kHz, and 2 recordings at 5, 10 and 15 kHz, across three rats. An AC magnitude of 50 micro amps was used, with the probe electrical signals being sinusoidal AC at the relevant frequency.

The results of this experiment are shown in FIG. 7 which plots frequency of the probe electrical signal in the abscissa, and the described signal to noise ratio (SNR) in the ordinate, with error bars of one standard error. It can be seen that below about 5 kHz and above about 12 kHz the SNR drops away, so that using a probe signal frequency in the range 5 to 12 kHz is advantageous. A peak is also clearly evident at around 6 kHz, so that using a probe signal; frequency in the range 4 to 8 kHz, or more particularly 5 to 7 kHz is advantageous. The inventors have also demonstrated experimentally that a peak in the signal to noise ratio occurs at around 10 kHz, so that probe signals with a frequency in the range of 9 to 11 kHz is also advantageous.

More generally, a probe signal frequency in the range of 1 to 20 kHz may be considered advantageous. These frequency ranges may be considered to be advantageous in carrying out electrical impedance tomography both on the sciatic nerve, and on other peripheral nerves in animal subjects, for example in mammal subjects including humans.

The above experimental and proposed frequency ranges for improved signal to noise ratio are particularly applicable in the case of myelinated axons. However, the inventors have also determined that the probe signal frequency ranges needed for improved signal to noise ratios maybe different for different types for nerve fibres, For example, for non-myelinated axons the inventors have demonstrated that probe electrical signals in the ranges of 1 to 2 kHz, or more broadly 0.5 to 3 kHz, and also from 4 to 5 kHz, or more generally from 4 to 7 kHz, are particularly advantageous for reducing the signal to noise ratios of the electrical responses and determined electrical properties.

In using probe signals with the above frequency ranges, demodulation of the collected signals is preferably carried out with a bandwidth of about +/−0.2 to 3.0 kHz around the carrier frequency in order to have a temporal resolution corresponding to the frequency of events to be detected in the nerve with a resulting optimized signal to noise ratio, for example with nerve events being detected at frequencies over a corresponding range of about 0.2 kHz to 3.0 kHz.

Although particular embodiments of the invention have been described, it will be apparent to the skilled person that various modifications and alterations can be made without departing from the scope of the invention. For example although it has been described in detail how probe signals may be applied to the peripheral nerve using electrodes, and resulting electrical signals collected using electrodes in contact with an outside surface of the nerve, other techniques may be used to inject the probe signal and/or to collect resulting electrical signals, including techniques not using electrodes such as by inductive and/or capacitative coupling.

Although the experiments described herein have used rat models, the experimental results and all aspects of the invention are considered to be relevant to human subjects and other mammals, and to other animals.

The invention claimed is:

1. A method of determining electrical properties in a peripheral nerve of a human or animal subject, comprising:
spacing a plurality of electrodes around a perimeter of, and in contact with the peripheral nerve;
for each of a plurality of combinations of said plurality of electrodes, applying a probe electrical signal to the electrodes of said plurality of combinations and measuring resulting electrical responses at one at one or more of said plurality of electrodes; and
using the electrical responses to determine electrical properties of the peripheral nerve within the perimeter by carrying out an electrical impedance tomography image reconstruction using the electrical responses to determine a map or image of electrical properties of a cross section of the peripheral nerve within said perimeter.

2. The method of claim 1, further comprising:
simultaneously applying the probe electrical signal to each of the plurality of combinations of said plurality of electrodes and simultaneously measuring said plurality of electrodes responses at one or more of said electrodes resulting from each of said plurality of combinations.

3. The method of claim 2 further comprising:
distinguishing between each of the plurality of combinations of the plurality of electrodes to which a probe electrical signal is applied simultaneously by using frequency division multiplexing between the plurality of combinations of the plurality of electrodes.

4. The method of claim 1, wherein the determined electrical properties are representative of impedance.

5. The method of claim 1, wherein the peripheral nerve is an autonomic nerve.

6. The method of claim 1, wherein the step of spacing the plurality of electrodes around the perimeter of the peripheral nerve comprises providing the plurality of electrodes on a flexible cuff and wrapping the flexible cuff around the perimeter of the peripheral nerve so that the plurality of electrodes are in contact with the perimeter of the peripheral nerve.

7. The method of claim 6, wherein the flexible cuff is secured around the peripheral nerve using a clamp provided with a slot, and electrical connectors to the plurality of electrodes extend through the slot.

8. The method of claim 1, wherein some or all of the plurality of electrodes are elongate along an axis of the peripheral nerve.

9. The method of claim 1, further comprising:
applying a modulation signal to said peripheral nerve, to modulate electrical activity of said peripheral nerve, dependent upon the determined electrical properties.

10. The method of claim 1, further comprising:
providing a signal representing a subject activity of the human or animal subject associated with electrical activity in the peripheral nerve;
determining, during the subject activity, the electrical properties of the peripheral nerve; and
comparing the signal representing the subject activity with the determined electrical properties to thereby identify one or more parts of the peripheral nerve within the perimeter which are associated with the subject activity.

11. The method of claim 10, wherein the subject activity comprises providing stimulation at one or more locations of the human or animal subject which are remote from the plurality of electrodes, to thereby determine one or more parts of the peripheral nerve within the perimeter which are associated with the one or more locations.

12. The method of claim 10 wherein the subject activity comprises autonomic or somatic activity of the human or animal subject.

13. The method of claim 10, wherein the subject activity comprises breathing activity of the human or animal subject.

14. The method of claim 10, further comprising:
applying a modulation signal specifically to one or more of said identified parts of the peripheral nerve dependent upon the determined electrical properties, to thereby modulate activity of the peripheral nerve.

15. The method of claim 1, wherein the probe electrical signal for one or more of the combinations of electrodes has a frequency in a range of 1 kHz to 20 kHz or in a range of 5 kHz to 12 kHz.

16. The method of claim 1, wherein the probe electrical signal for one or more of the combinations of electrodes has a frequency in a range of 4 kHz to 8 kHz or in a range of 5 kHz, or in a range of 9 kHz to 11 kHz.

17. The method of claim 1, wherein the probe electrical signal for one or more of the combinations of electrodes has a frequency in a range of 4 kHz to 5 kHz.

18. The method of claim 1 wherein the determined electrical properties of the peripheral nerve within the perimeter comprise electrical activity within the peripheral nerve.

19. A method of imaging a cross section of electrical activity within a peripheral nerve, the method comprising:
disposing a plurality of electrodes around a perimeter of, and in contact with, the peripheral nerve,
applying a probe electrical signal to each of a plurality of combinations of the plurality of electrodes, and measuring resulting electrical responses at one or more of said plurality of electrodes; and
using the resulting electrical responses to determine electrical activity of the peripheral nerve within the perimeter by carrying out electrical impedance tomography image reconstruction to determine a map or image of electrical activity of a cross section of the peripheral nerve within said perimeter.

20. The method of claim 19 wherein the peripheral nerve is an autonomic nerve.

\* \* \* \* \*

UNITED STATES PATENT AND TRADEMARK OFFICE
CERTIFICATE OF CORRECTION

PATENT NO. : 11,006,881 B2
APPLICATION NO. : 15/567537
DATED : May 18, 2021
INVENTOR(S) : Holder et al.

It is certified that error appears in the above-identified patent and that said Letters Patent is hereby corrected as shown below:

On the Title Page

Item [30]: delete "1506760" and insert -- 1506760.6 --
Item [30]: delete "1509503" and insert -- 1509503.7 --

In the Specification

Column 2, Line 64: insert a paragraph break in between "ratio." and "To"

In the Claims

Column 18, Line 52, Claim 17: "frequency in a range of 4 kHz to 5 kHz." and insert -- frequency in a range of 1 kHz to 2 kHz, and/or in a range of 4 kHz to 5 kHz. --

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*